United States Patent [19]

Thornton

[11] Patent Number: 4,908,203

[45] Date of Patent: Mar. 13, 1990

[54] METHOD FOR INDUCING HIV NEUTRALIZING ANTIBODIES USING AN INTERNAL IMAGE IDIOTOPE

[75] Inventor: George B. Thornton, Rancho Bernardo

[73] Assignee: Johnson & Johnson, New Brunswick, N.J.

[21] Appl. No.: 95,467

[22] Filed: Sep. 9, 1987

[51] Int. Cl.$^4$ .................... A61K 39/00; A61K 39/42; A61K 45/02; G01N 33/53
[52] U.S. Cl. .................................... 424/86; 424/85.8; 530/388; 530/812; 514/21; 514/885; 436/547
[58] Field of Search ................ 424/86, 85.8; 530/387, 530/388, 810, 812; 814/21, 885; 436/547

[56] References Cited

PUBLICATIONS

Chanh et al, "Monoclonal Anti-Idiotypic Antibody Mimics the CD4 Receptor and Binds Human Immunodeficiency Virus", *Proc. Natl Acad Sci*, USA, vol. 84, pp. 3891–3895, Jun. 1987.

Zhou et al, "Mouse Monoclonal Anti-Anti-CD$_4$ Antibodies Recognize Human Immuno-Deficiency Virus Antigens", *FASEB*, 46:1352 (1987).

Chanh et al, "Anti-Idiotypic Antibodies Against OKTYA Bind to Human Immuno-Deficiency Virus", *FASEB*, 46:1352 (1987).

*Primary Examiner*—John Kight
*Assistant Examiner*—Nathan M. Nutter
*Attorney, Agent, or Firm*—Dressler, Goldsmith, Shore, Sutker & Milnamow, Ltd.

[57] ABSTRACT

The present invention contemplates a method for inducing a HIV neutralizing immune response using an OKT4A antibody molecule homolog as an immunogen. Vaccines for practicing an immunization method of this invention are also described.

6 Claims, 2 Drawing Sheets

METHOD FOR INDUCING HIV NEUTRALIZING ANTIBODIES USING AN INTERNAL IMAGE IDIOTOPE

DESCRIPTION

1. Technical Field

The present invention contemplates the use of an anti-CD4 antibody expressing an internal image idiotope that immunologically mimics a HIV antigenic determinant as an immunogen to produce human immunodeficiency virus (HIV) neutralizing antibodies. Also contemplated is a vaccine comprising antibodies expressing a HIV internal image idiotope.

2. Background

The etiological agent of acquired immunodeficiency syndrome (AIDS) is the human immunodeficiency virus [HIV; also called human T-lymphotropic virus type III (HTLV-III), lymphadenopathy-associated virus (LAV), and AIDS-associated retrovirus (ARV)]. HIV infection is mediated by a 62,000 molecular weight receptor protein on the surface of T lymphocytes (T cells) that is known in the art as the CD4 or T4 antigen. See Terhorst et al., Science, 209:520 (1980) and Dalgleish et al., Nature. 312:763-8 (1984). The site on HIV bound by CD4 has been identified as being on the external envelop glycoprotein (EGP) having a molecular weight of 120,000. McDougal et al., Science, 231:382-385 (1985). Guyader et al., Nature, 326:662-669 (1987) have postulated that presentation of the CD4 binding domain on the HIV EGP out of context of the virion, that is, its presentation as a peptide, might induce a virus neutralizing antibody response. Therefore, if the CD4 binding domain could be identified and molecularly mimicked, such a mimic might serve as a potential HIV vaccine.

The development of a safe and effective vaccine against HIV infection is one of the highest priorities of public health officials. One important issue in the effort to develop a vaccine is the type of vaccine preparation that should be developed. There is an understandable reluctance to use inactivated or killed whole virus preparations because of the possibility that nucleic acid of the killed virus could still be integrated into the genome of the host's cells with the possibility of ensuing viral replication. Virus subunits and synthetic polypeptides corresponding in sequence to various viral proteins are currently being examined for immunogenicity in laboratory animals. However, there is concern that even the glycosylated recombinant subunits produced from mammalian vectors will not present antigenic determinants to the immune system in a manner that would elicit effective immunity.

Another approach to HIV vaccine preparation that avoids the above-discussed problems associated with subunit and synthetic peptide based vaccines is the use of antibodies that express internal image idiotopes. Idiotopes are antigenic determinants (epitopes) expressed by an antibody molecule. Internal image idiotopes are antigenic determinants expressed by an antibody molecule that are immunologically similar or identical to antigenic determinants found on an antigen that is foreign or external to the immune system.

The operational theory explaining the immunologic similarity of an internal image idiotope and its corresponding external antigenic determinant is that the internal image idiotope is a conformational homolog of the external antigenic determinant. Because they are conformationally homologous, an internal image idiotope and its corresponding external antigenic determinant are immunologically cross reactive, i.e., an antibody induced by one will immunoreact with the other. Therefore, an antibody expressing an internal image idiotope corresponding to an external antigenic determinant expressed by an infectious agent can be substituted for the infectious agent in a vaccine.

The production of an antibody expressing an internal image corresponding to an antigenic determinant on an infectious agent requires finding or producing an immunogenic "template" that can induce the internal image bearing antibody. Templates for producing internal image antibodies are immunogenic molecules having at least a portion of their conformation that is complementary to or the mirror image of the antigenic determinant of interest. The conformational relationship between an internal image, its template and its homologous antigenic determinant is illustrated in FIG. 1.

For infectious agents, template bearing molecules used by the art to induce internal imagebearing antibodies are proteins that bind the infectious agent of interest. Such proteins include antibody molecules whose antibody combining sites immunoreact with the infectious agent of interest and cell surface receptor proteins that bind the infectious agent. In either case, the critical feature of the binding protein is that portion of its structure that interacts with the infectious agent because it is only that portion that can act as template.

For instance, Reagan et al., J. Virol., 48:660-6 (1983) obtained five monoclonal antibodies whose antibody combining sites immunoreacted with rabies virus. Each of the monoclonals was used as an immunogen to induce an anti-idiotypic antibody, i.e., an antibody that immunoreacts with an idiotope. Only two of the five anti-idiotypic antibodies were found to be capable of inducing anti-anti-idiotypic antibodies that immunoreacted with and neutralized rabies virus. That is, only two of the five anti-idiotypic antibodies expressed an immunogenic internal image idiotope corresponding to a rabies virus antigenic determinant. Reagan et al. indicated that one reason at least two of the anti-idiotypic antibodies failed to express internal image idiotopes was because the monoclonal antibody idiotopes that induced them were not in the monoclonal antibody combining site, i.e., the monoclonal idiotopes (templates) that induced the anti-idiotypic antibodies were not involved in virus binding.

The ability of a cell surface receptor protein to act as a template for inducing internal image-bearing antibodies against HIV was suggested by the present inventor and was reported by T.C. Chanh on Sept. 9, 1986 during the meeting on Modern Approaches to New Vaccines at the Cold Spring Harbor Laboratories, Cold Spring Harbor, N.Y. A more detailed discussion of that study appears in Chanh et al., Proc. Natl. Acad. Sci. U.S.A., 84:3891-95 (1987). According to the latter report, Chanh et al., obtained 3 monoclonal antibodies, anti-Leu-3a, OKT4A and anti-T4, that had been raised against CD4, the T cell receptor for HIV. Anti-Leu-3a was used as an immunogen to induce an anti-idiotypic monoclonal antibody, designated HF1.7. HF1.7 was then shown to be capable of immunoreacting to about the same extent with the antibody combining sites of anti-Leu-3a and OKT4A, and to a somewhat lesser extent with the combining site of anti-T4, indicating that at least some of the anti-Leu-3a and OKT4A antibody combining sites have significant conformational homology, i.e., were induced by a similar or identical CD4 determinant. In addition, HF1.7 was shown to be capable of immunoreacting with and neutralizing HIV, indicating that the antigenic determinant on CD4 recognized by anti-Leu-3a has a conformation that is complementary to an antigenic determinant on HIV. These results indicate that the CD4 antigenic determinant recognized by monoclonal antibody anti-Leu-3a, can be used as a template to induce internal image-bearing antibodies that can substitute for HIV in vaccine preparations. See FIG. 2.

More recently, Chanh et al., FASEB, 46:1352 (1987) have reported that baboons immunized with OKT4A monoclonal antibodies, which have been commercially available since at least 1984, produced anti-idiotypic antibodies, i.e., anti-OKT4A antibodies, characterized by their ability to immunoreact with OKT4A and anti-Leu-3 a monoclonal antibodies and HIV antigens. In addition, Zhou et al., FASEB, 46:1352 (1987) reported using OKT4A monoclonal antibody molecules as an immunogen to induce anti-HIV antibodies in mice.

Taken together, the above discussed reports demonstrate that CD4, the T cell receptor for HIV, expresses an antigenic determinant that can be used as a template to produce internal image-bearing antibodies that immunologically mimic an antigenic determinant on HIV. The CD4 antigenic determinant(s) that can act as template for the production of internal image antibodies is involved in the CD4-HIV binding reaction and induced the anti-Leu-3a and OKT4A antibody combining sites. In addition, those reports also indicate that at least some portion of the antibody combining sites of monoclonal antibodies anti-Leu-3a and OKT4A are conformationally homologous and that it is that homologous portion that is responsible for inducing anti-HIV antibodies.

BRIEF SUMMARY OF THE INVENTION

It has now been found that antibody molecules having an antibody combining site conformationally homologous to the antibody combining site of the IgG2A anti-CD4 antibody produced by hybridoma OKT4A can be used to induce HIV neutralizing antibodies. Thus, the present invention contemplates a method for inducing HIV neutralizing antibodies comprising administering an immunologically effective amount of an OKT4A homolog.

In addition, the present invention contemplates a vaccine capable of inducing HIV neutralizing antibodies comprising an immunologically effective amount of an OKT4A homolog operatively linked to an immunogenic carrier.

Also contemplated is a vaccine capable of inducing HIV neutralizing antibodies comprising, in admixture, immunologically effective amounts of both an OKT4A homolog and an immunopotentiator suitable for human use.

When the template is on an antibody combining site (Ab-1), the internal image is said to be on an anti-idiotope or anti-idiotypic antibody combining site (Ab-2). Ab-2 and the epitope that induced Ab-1 will therefore have homologous conformations.

When the template is a binding site on a cellular receptor, the internal image will be on an anti-receptor antibody combining site. The protein binding site and the anti-receptor antibody combining site will therefore have homologous conformations.

Figure 1:
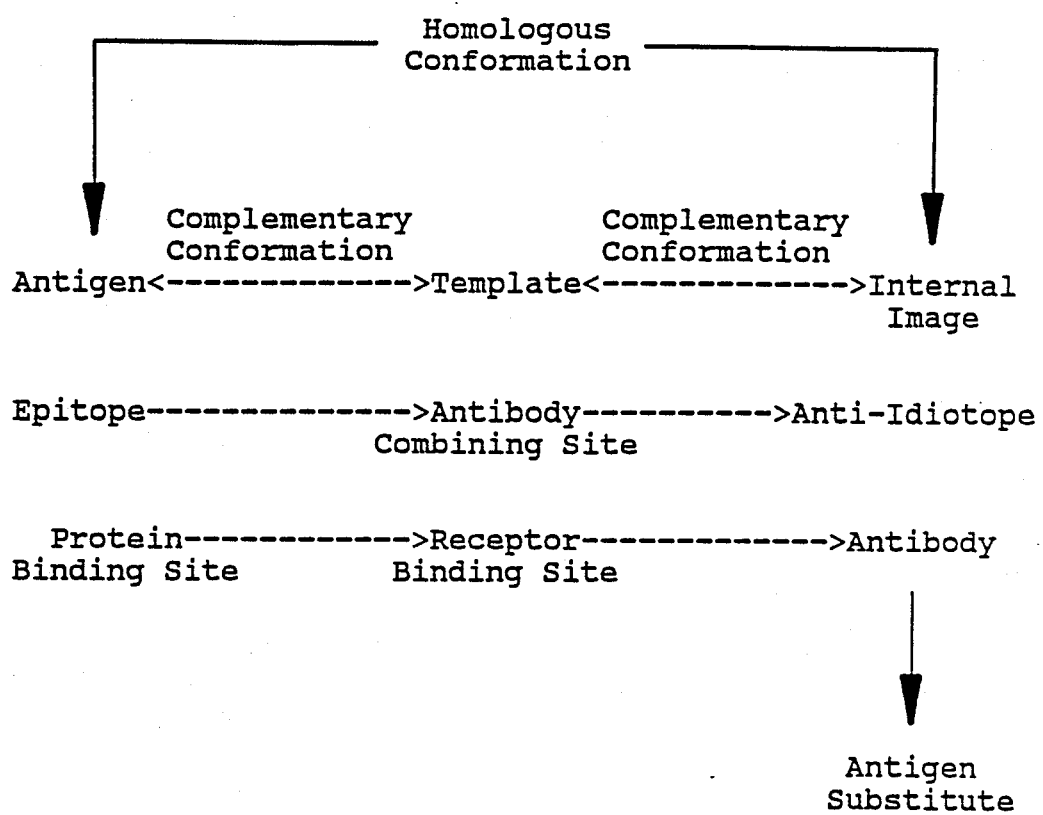
FIG. 1 illustrates the conformational relationship of the various molecular entities discussed herein. An antigen present as part of an infectious agent contains an epitope or protein binding site whose structure can be mimicked by an internal image idiotope. A template is a portion of a protein that binds an infectious agent (viral antigen) and therefore has a conformation that is complementary to a portion of the antigen. The template also has a conformation that is complementary to the internal image idiotope bearing antibody combining site it induces. Because the internal image idiotope and the antigen have conformations that are complementary to the same template, they have a similar or homologous conformation.
Figure 2:
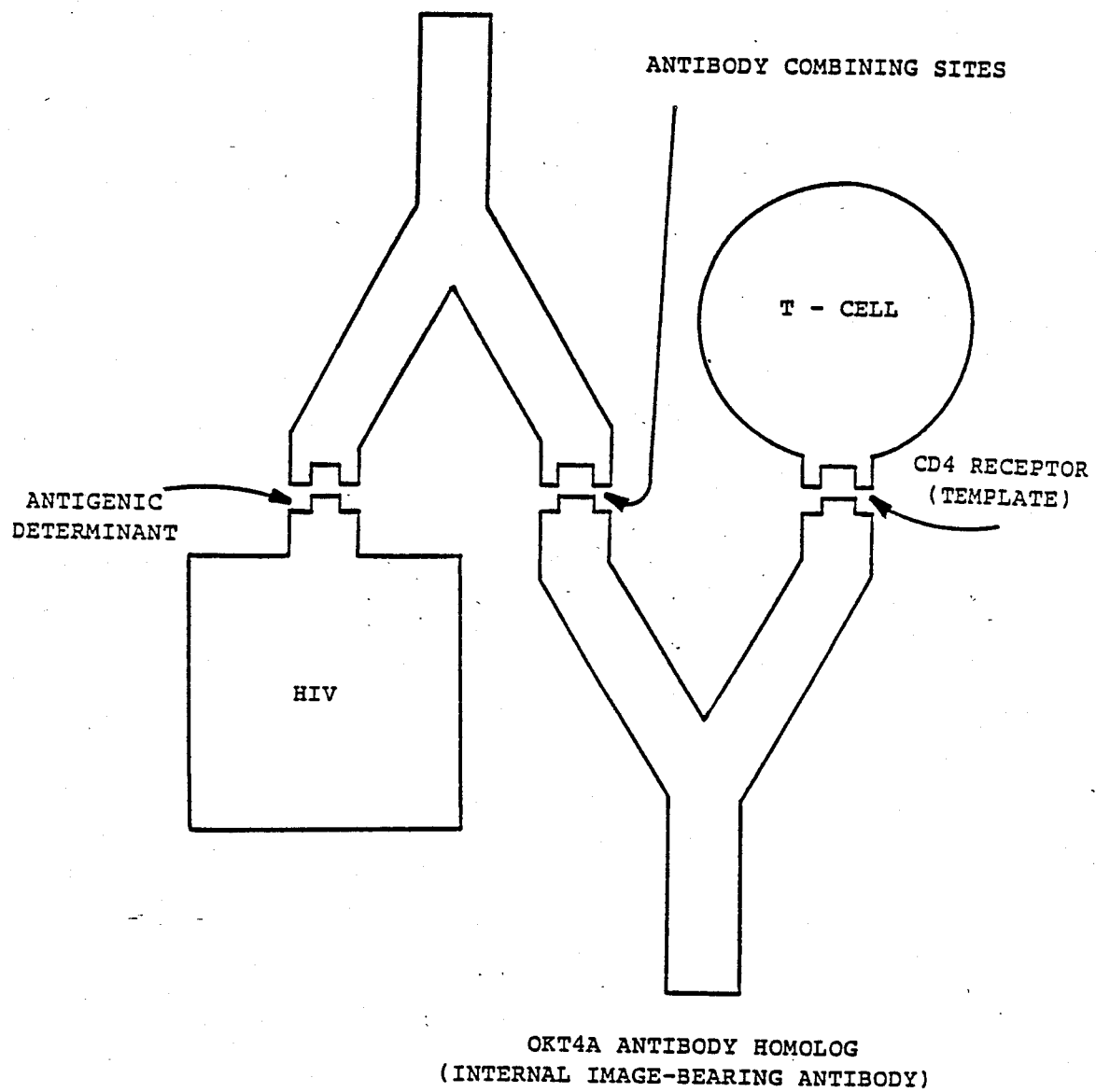

FIG. 2 is a schematic representation that further illustrates the complementary conformations pertinent to the present invention. In this schematic, HIV is represented by the rectangle with a protrusion that represents an HIV antigenic determinant or antigen. A HIV-neutralizing antibody induced by an OKT4A homolog is illustrated with two antibody combining sites that are complementary (1) to the HIV antigenic determinant (antigen), and (2) to the combining site of an OKT4A antibody homolog. A second OKT4A antibody homolog combining site is shown to be of complementary conformation to the CD4 receptor of a T-cell; the T-cell being represented by a circle with a protrusion having an indentation (the CD4 receptor). This schematic also illustrates that the CD4 receptor and HIV-neutralizing antibody combining site are of a homologous conformation, as are the OKT4A antibody homolog combining site and the HIV antigenic determinant.

DETAILED DESCRIPTION OF THE INVENTION

The present invention contemplates methods and compositions employing an OKT4A antibody molecule homolog.

The term "antibody" in its various grammatical forms is used herein to refer to immunoglobulin molecules and immunologically active portions of immunoglobulin molecules, i.e., molecules that contain an antibody combining site or paratope. Exemplary antibody molecules are intact immunoglobulin molecules, substantially intact immunoglobulin molecules, and those portions of an immunoglobulin molecule that contain the paratope, including those portions known in the art as Fab, Fab', F(ab')2 and F(v).

An OKT4A antibody molecule homolog, i.e., an OKT4A homolog, contains a paratope whose structure is defined by the ability to:

(1) immunoreact with the CD4 antigen of helper/inducer T lymphocytes to form a OKT4A-CD4 complex that does not bind HIV, and (2) induce antibody molecules that immunoreact with:
  (a) HIV to form a HIV-antibody molecule complex that does not bind CD4, and
  (b) the IgG2A anti-CD4 antibody molecules produced by hybridoma OKT4A that was deposited on Sept. 9, 1987 with the American Type Culture Collection (ATCC), 12301 Parklawn Dr., Rockville, Md. 20852 and has the ATCC accession number HB9526 OKT4A monoclonal antibody is commercially available from Ortho Pharmaceutical, Inc., Raritan, N.J.

A preferred homolog is the IgG2A anti-CD4 antibody molecule characterized as being capable of being produced by the above described deposited hybridoma OKT4A. More preferred is a paratope-containing fragment of the IgG2A anti-CD4 antibody molecule capable of being produced by hybridoma OKT4A.

OKT4A antibody molecules are typically produced by culturing hybridoma OKT4A in a growth medium for a time period sufficient for the hybridoma cells to produce and secrete into the medium IgG2A anti-CD4 antibodies. The antibody molecule-containing medium is then collected and, if desired, the antibody molecules are isolated therefrom using well known techniques.

Media useful for culturing hybridoma OKT4A are both well known in the art and commercially available and include synthetic culture media, inbred mice and the like.

Hybridomas producing OKT4A homologs can be produced using well known methods. Exemplary methods have been described by Bach et al., *J. Immunol.*, 127:980-82 (1981), and Rao et al., *Cell. Immunol.*, 80:310-19 (1983). See generally, Kung et al., *Transplant. Proc.*,XII (Suppl. 1):141 (1980). See also Chanh et al., *Proc. Natl. Acad. Sci. U.S.A.*, 84:3891-3895 91987) for screening methods.

Methods for preparing paratope-containing portions of immunoglobulin molecules such as Fab, Fab', F(ab')2 and F(v) from substantially intact antibodies are well known. See, for example, U.S. Pat. No. 4,342,566, Inbar et al., *Proc. Natl. Acad. Sci. U.S.A.*. 69:2659-62 (1972), and Goding, *Monoclonal Antibodies: Principles and Practice*, Academic Press, p118-124 (1983).

A. Methods for Producing HIV-Neutralizing Antibodies

The present invention provides a method for inducing HIV neutralizing antibodies comprising administering to a mammal an immunologically effective amount of an OKT4A homolog.

Typical mammals used in practicing a method of this invention include mice, rabbits, goats, primates, humans and the like.

By "immunologically effective amount" is meant an amount sufficient to induce in the mammal an amount of HIV neutralizing antibodies detectable by viral infectivity assay methods. Viral infectivity assay methods for assaying for the presence and/or amount of HIV neutralizing antibodies in a body fluid sample are well known in the art. See, for example, Chanh et al., *EMBO*, 5:3065–71 (1986).

The immunologically effective amount of OKT4A homolog per unit dose depends on, among other things, the species of mammal inoculated, the body weight of the mammal and the chosen inoculation regimen as is well known in the art. Inocula typically contain OKT4A homolog concentrations of about 10 micrograms (ug) to about 500 milligrams (mg), preferably about 1 mg to about 10 mg and more preferably about 5 mg per inoculation (dose).

In preferred vaccination regimens about 1 mg to about 5 mg, preferably about 5 mg, of OKT4A homolog is administered daily for about 10 to about 20 days, preferably about 15 days.

In preferred embodiments, an inoculation method of this invention uses an OKT4A homolog that is a substantially intact immunoglobulin molecules. Preferably, the OKT4A homolog used as immunogen is one characterized as capable of being produced by the hybridoma OKT4A. Also preferred is the use of a OKT4A homolog in the form of a Fab, F(ab')2 and F(v) immunoglobulin fragment, alone or in combination, to induce HIV neutralizing antibodies.

Preferably, the OKT4A homolog is administered in substantially pure form. As used herein, the phrase "substantially pure" in relation to antibody molecules means that, within serologically detectable limits, only one species of antibody combining site capable of binding CD4 is present. Thus, while a substantially pure antibody molecule preparation may contain more than one species of antibody combining site, such a preparation displays a single binding affinity for CD4. An antibody molecule in substantially pure form is typically designated a "monoclonal antibody" by those skilled in the art because such compositions are usually produced using monoclonal hybridoma cultures.

B. Vaccines

A vaccine of the present invention comprises an immunologically effective amount of a OKT4A antibody molecule homolog operatively linked to an immunogenic carrier.

As used herein, the term "operatively linked" means that the OKT4A homolog and carrier protein are physically associated by a linking means that does not interfere with the ability of either of the linked groups to function as described. Because immunogenic carriers are typically proteins themselves, the techniques of protein conjugation or coupling through activated functional groups is particularly applicable For a review of those techniques, see Aurameas et al., *Scand. J. Immunol.*, Vol. 8, Supp-1, 7–23 (1978). See also U.S. Pat. Nos. 4,493,795 and 4,671,958.

Useful immunogenic carriers are well known in the art and are generally large proteins. Exemplary of such carriers are keyhold limpet hemocyanin (KLH), edestin, thyroglobulin, albumins such as bovine serum albumin (BSA) or human serum albumin (HSA), red blood cells such as sheep erythrocytes (SRBC), tetanus toxoid, cholera toxoid as well as polyamino acids such as poly (D-lysine: D-glutamic acid), and the like.

The choice of carrier is more dependent upon the ultimate use of the inoculum and is based upon criteria not particularly involved in the present invention. For example, a carrier that does not generate an untoward reaction in the particular mammal to be inoculated should be selected.

In another embodiment, a vaccine of the present invention comprises an admixture of immunologically effective amounts of (1) an OKT4A homolog, and (2) an immunopotentiator suitable for human use.

As used herein, an "immunopotentiator" is a molecular entity that stimulates maturation, differentiation and function of B and/or T lymphocytes. Immunopotentiators are well known in the art and include T cell stimulating polypeptides such as those described in U.S. Pat. No. 426,324 and the C8-substituted guanine nucleosides described by Goodman et al., *J. Immunol.*, 135:3284–88 (1985) and U.S. Pat. No. 4,643,992.

The phrases "suitable for human use" and "pharmaceutically acceptable" refer to molecular entities and compositions that do not produce an allergic or similar untoward reaction when administered to a human.

The preparation of a vaccine that contains an antibody molecule as an active ingredient is well understood in the art. Typically, such vaccines are prepared as injectables, either as liquid solutions or suspensions; solid forms suitable for solution in, or suspension in, liquid prior to injection may also be prepared. The preparation can also be emulsified.

The active immunogenic ingredient is dissolved, dispersed or admixed in an excipient that is pharmaceutically acceptable and compatible with the active ingredient as is well known. Suitable excipients are, for example, water, saline, phosphate buffered saline (PBS), dextrose, glycerol, ethanol, or the like and combinations thereof. In addition, if desired, the vaccine can contain minor amounts of auxiliary substances such as wetting or emulsifying agents, pH buffering agents or adjuvants which enhance the effectiveness of the vaccine. A preferred embodiment contains about 1 mg to about 5 mg OKT4A homolog protein, exclusive of carrier, in about 1 ml PBS.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the rage of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders and contain 10%-95% of active ingredient, preferably 25-70%.

An OKT4A homolog can be formulated into a vaccine as a neutral or salt form. Pharmaceutically acceptable salts, include the acid addition salts (formed with the free amino groups of the antibody) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine, and the like.

The vaccines are administered in a manner compatible with the dosage formulation, and in such amount as will be therapeutically effective and immunogenic. The quantity to be administered depends on the subject to be treated, capacity of the subject's immune system to synthesize antibodies, and degree of protection desired. Precise amounts of active ingredient required to be administered depend on the judgement of the practitioner and are peculiar to each individual. However, suitable dosage ranges are of the order of about one hundred micrograms to about one hundred milligrams, preferably about one to about 10 milligrams and more preferably about 5 milligrams active ingredient per individual. Suitable regimes for initial administration and booster shots are also variable, but are typified by an initial administration followed in one or two week intervals by a subsequent injection or other administration.

A vaccine can also include an adjuvant as part of the excipient. Adjuvants such as complete Freund's adjuvant (CFA), incomplete Freund's adjuvant (IFA) for use in laboratory mammals are well known in the art. Pharmaceutically acceptable adjuvants such as alum can also be used. An exemplary vaccine thus comprises one ml of phosphate buffered saline (PBS) containing about 1 mg to about 5 mg OKT4A homolog adsorbed onto about 0.5 mg to about 2.5 mg of alum. A preferred vaccine comprises 1 ml of PBS containing 1 mg OKT4A homolog adsorbed onto 2.5 mg of alum.

C. Anti-Idiotypic Antibody Compositions

An anti-idiotypic antibody molecule of the present invention is an antibody molecule that immunoreacts with an OKT4A homolog paratope and HIV. An anti-idiotypic antibody composition of the present invention is therefore characterized as containing antibody molecules that 1) immunoreact with an OKT4A homolog antibody combining site, and 2) immunoreact with and neutralize HIV.

The preparation of anti-idiotypic antibodies against a monoclonal antibody combining site is well known in the art. See Staudt et al., *J. Exp. Med.*, 157:687–704 (1983), and Regan et al., supra. Briefly, to produce an anti-idiotypic antibody composition of this invention, a laboratory mammal is inoculated with an immunologically effective amount of an OKT4A homolog, typically as present in a vaccine of the present invention. The anti-OKT4A homolog antibody molecules thereby induced are then collected from the mammal and those immunospecific for both the OKT4A paratope and HIV are isolated to the extent desired by well known techniques such as, for example, by immunoaffinity chromatography. The anti-idiotypic antibody composition so produced can be used in, inter alia, the diagnostic methods and systems of the present invention to detect HIV in a body sample.

Monoclonal anti-idiotypic antibody compositions are also contemplated by the present invention. A monoclonal anti-idiotypic antibody composition contains, within detectable limits, only one species of antibody combining site capable of effectively immunologically binding an OKT4A homolog paratope ad HIV. Thus, a monoclonal anti-idiotypic antibody composition of the present invention typically displays a single binding affinity for HIV and a single binding affinity for HIV.

Suitable antibodies in monoclonal form, typically whole antibodies, can also be prepared using hybridoma technology described by Reagan et al., *Proc. Natl. Sci., U.S.A.*, 84:3891–95 (1987), which description is incorporated herein by reference. Briefly, to form the hybridoma from which the monoclonal anti-idiotypic antibody composition is produced, a myeloma or other self-perpetuating cell line is fused with lymphocytes obtained from the spleen of a mammal hyperimmunized with an OKT4A homolog.

It is preferred that the myeloma cell line be from the same species as the lymphocytes. Typically, a mouse of the strain 129 G1X$^+$ is the preferred mammal. Suitable mouse myelomas for use in the present invention include the hypoxanthine-aminopterin-thymidine-sensitive (HAT) cell lines P3X63-Ag8.653, and Sp2/0-Ag14 that are available from the American Type Culture Collection, Rockville, Md., under the designations CRL 1580 and CRL 1581, respectively.

Splenocytes are typically fused with myeloma cells using polyethylene glycol (PEG) 1500. Fused hybrids are selected by their sensitivity to HAT. Hybridomas secreting the anti-idiotypic antibody molecules of this invention are identified using serological methods such as a commercially available enzyme linked immunosorbent assay (ELISA) diagnostic kit for detecting antibodies to HIV.

A monoclonal anti-idiotypic antibody composition of the present invention can be produced by initiating a monoclonal hybridoma culture comprising a nutrient medium containing a hybridoma that secretes antibody molecules of the appropriate anti-OKT4A specificity. The culture is maintained under conditions and for a time period sufficient for the hybridoma to secrete the antibody molecules into the medium. The antibody-containing medium is then collected. The anti-OKT4A paratope antibody molecules can then be further isolated by well known techniques.

Media useful for the preparation of these compositions are both well known in the art and commercially available and include synthetic culture media, inbred mice and the like. An exemplary synthetic medium is Dulbecco's minimal essential medium (DMEM; Dulbecco et al., Virol. 8:396 (1959)) supplemented with 4.5 gm/1 glucose, 20 mm glutamine, and 20% fetal calf serum. An exemplary inbred mouse strain is the Balb/c.

The monoclonal anti-idiotypic antibody compositions produced by the above method can be used, for example, in diagnostic and therapeutic modalities wherein formation of a HIV-containing immunoreaction product is desired.

D. Diagnostic Systems

A diagnostic system in kit form of the present invention includes, in an amount sufficient for at least one assay, an anti-idiotypic antibody composition or monoclonal anti-idiotypic antibody composition of the present invention, as a packaged reagent. Instructions for use of the packaged reagent are also typically included.

As used herein, the term "package" refers to a solid matrix or material such as glass, plastic, paper, foil and the like capable of holding within fixed limits an anti-idiotypic antibody composition or monoclonal anti-idiotypic antibody composition of the present invention. Thus, for example, a package can be a glass vial used to contain milligram quantities of a contemplated anti-idiotypic antibody or it can be a microtiter plate well to which microgram quantities of a contemplated anti-idiotypic antibody have been operatively affixed, i.e., linked so as to be capable of being immunologically bound by HIV.

"Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing an anti-idiotypic antibody molecule of the present invention.

The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an anti-idiotypic antibody molecule of the present invention, or used separately, and those atoms or molecules can be used alone or in conjunction with additional reagents. Such labels are themselves well-known in clinical diagnostic chemistry and constitute a part of this invention only insofar as they are utilized with otherwise novel proteins methods and/or systems.

The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyanate (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in Antibody As a Tool, Marchalonis, et al., eds., John Wiley & Sons, Ltd., pp. 189-231 (1982), which is incorporated herein by reference.

In preferred embodiments, the indicating group is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2,-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such as indium or $^{3}H$.

The linking of labels, i.e., labeling of, proteins is well known in the art. For instance, anti-idiotypic antibody molecules produced by a hybridoma can be labeled by metabolic incorporation of radioisotope-containing amino acids provided as a component in the culture medium. See, for example, Galfre et al., Meth. Enzymol., 73:3-46 (1981). The techniques of protein conjugation or coupling through activated functional groups are particularly applicable. See, for example, Aurameas-, et al., Scand. J. Immunol., Vol. 8 Suppl. 7:7-23 (1978), Rodwell et al., Biotech., 3:889-894 (1984), and U.S. Pat. No. 4,493,795.

The diagnostic systems can also include, preferably as a separate package, a specific binding agent. A "specific binding agent" is a molecular entity capable of selectively binding a reagent of the present invention or a complex containing such a species, but is not itself an anti-idiotypic antibody molecule of the present invention. Exemplary specific binding agents are second antibody molecules, complement proteins or fragments thereof, S. aureus protein A, and the like. Preferably the specific binding agent binds the reagent species when that species is present as part of a complex.

In preferred embodiments, the specific binding agent is labeled. However, when the diagnostic system includes a specific binding agent that is not labeled, the agent is typically used as an amplifying means or reagent. In these embodiments, the labeled specific binding agent is capable of specifically binding the amplifying means when the amplifying means is bound to a reagent speciescontaining complex.

The diagnostic kits of the present invention can be used in an "ELISA" format to detect the presence or quantity of at least HIV in a body fluid sample such as serum, plasma or urine. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4the Edition of *Basic and Clinical Immunology* by D.P. Sites et al., published by Lange Medical Publications of Los Altos, Calif. in 1982 and in U.S. Pat. Nos. 3,654,090; No. 3,850,752; and No. 4,016,043, which are all incorporated herein by reference.

Thus, in preferred embodiments, an anti-idiotypic antibody molecule composition or monoclonal antibody molecule composition of the present invention can be affixed to a solid matrix to form a solid support that comprises a package in the subject diagnostic systems.

The reagent is typically affixed to the solid matrix by adsorption from an aqueous medium although other modes of affixation, well known to those skilled in the art, can be used.

Useful solid matrices are also well known in the art. Such materials are water insoluble and include the cross-linked dextran available under the trademark SEPHADEX from Pharmacia Fine Chemicals (Piscataway, N.J.); agarose; beads of polystyrene beads about 1 micron to about 5 millimeters in diameter available from Abbott Laboratories of North Chicago, Ill.; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The reagent labeled specific binding agent or amplifying reagent of any diagnostic system described herein can be provided in solution, as a liquid dispersion or as a substantially dry power, e.g., in lyophilized form. Where the indicating means is an enzyme, the enzyme's substrate can also be provided in a separate package of a system. A solid support such as the before-described microtiter plate and one or more buffers can also be included as separately packaged elements in this diagnostic assay system.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like.

EXAMPLES

The following examples are intended to illustrate, but not limit, the present invention.

1. OKT4A Antibody Molecule Production

Hybridoma OKT4A is cultured in a 5% $CO_2$, humidified atmosphere at 37 degrees C. in Dulbecco's Modified Eagles Medium (DMEM) containing 2 millimolar (mM) L-glutamine, 50 micrograms (ug) per ml gentamycin, 10% fetal bovine serum, 10% horse serum, all from Grand Island Biological Co., Lawrence, Mass., 10% NCTC medium from Microbiological Associates, Rockville, Md., 1 mM hypoxanthine and 0.3 mM thymidine, both from Sigma Chemical Corp., St. Louis, Mo. Cell concentration is kept in the range of about $1-2 \times 10^5$ cells per ml of medium to about $1-2 \times 10^6$ cells per ml of medium for cell growth, division, and production of antibody.

To produce ascites tumor fluid containing OKT4A antibody molecules, 10-week old Balb/c mice are immunologically primed by intraperitoneal injection with 0.3 ml of mineral oil and subsequently intraperitoneally injected with $3-5 \times 10^5$ OKT4A hybridoma cells. The inoculated mice are then maintained for a time period sufficient for OKT4A antibody-containing ascites tumor fluids to accumulate, e.g., for about 10 to about 21 days. The ascites fluid is collected and clarified by centrifugation at $15,000 \times g$ for 1 hour at 4 degrees C. and stored frozen at $-20$ degrees C.

OKT4A antibody molecules are isolated from the ascites fluid by subjecting the fluid to fast protein liquid chromatography (FPLC) on a Pharmacia Mono QHR 5/5 anion exchange column in a Pharmacia FPLC System (both from Pharmacia, Inc., Piscataway, N.J.) using a 0–0.5 M NaCl gradient in 10 mM Tris, pH 8.0, and following the directions supplied with the column. The OKT4A antibody molecules so isolated can then be transferred to any physiologically tolerable diluent desired by dialysis.

Alternatively, OKT4A antibody molecules can be isolated from the ascites tumor fluid by precipitation with ammonium sulfate according to the method described by Goding, *Monoclonal Antibodies: Principles and Practice*, Academic Press, p100–101 (1983). Briefly, that method entails slowly admixing saturated ammonium sulfate to the ascites fluid until about a 45% to about a 50% ammonium sulfate concentration is achieved. The precipitated immunoglobulins are then collected by centrifugation at $2000 \times g$, preferably $10,000 \times g$. The precipitate is washed 2 or 3 times in 40% saturated ammonium sulfate. The precipitated OKT4A antibody molecules are then dialyzed against 500–1000 volumes of phosphate buffered saline or any other physiologically tolerable diluent desired to remove ammonium sulfate. The dialysis fluid is changed several times at intervals of a few hours.

The foregoing specification, including the specific embodiments and examples, is intended to be illustrative of the present invention and is not to be taken as limiting. Numerous other variations and modifications can be effected without departing from the true spirit and scope of the present invention.

What is claimed is:

1. A method for inducing HIV neutralizing antibodies comprising administering an immunologically effective amount of an OKT4A antibody molecule homolog.

2. The method according to claim 1 wherein said OKT4A antibody molecule homolog is capable of being produced by the hybridoma having ATCC accession number HB9526.

3. The method according to claim 1 wherein said OKT4A antibody molecule homolog is in the form of an immunoglobulin Fab fragment.

4. The method according to claim 1 wherein said OKT4A antibody molecule homolog is in substantially pure form.

5. A composition comprising an immunologically effective amount of an OKT4A antibody molecule homolog operatively linked to a carrier protein dispersed in a pharmaceutically acceptable excipient.

6. A composition comprising immunologically effective amounts of an OKT4A antibody molecule homolog and an immunoproteinator suitable for human use admixed in a pharmaceutically acceptable excipient.

* * * * *